United States Patent [19]

Stafford

[11] Patent Number: 5,184,365
[45] Date of Patent: Feb. 9, 1993

[54] METHOD AND APPARATUS OF A POSITIONING SYSTEM FOR AIRWAY MANAGEMENT

[75] Inventor: Timothy J. Stafford, Boston, Mass.

[73] Assignee: Trustees of Boston University, Boston, Mass.

[21] Appl. No.: 626,583

[22] Filed: Dec. 7, 1990

[51] Int. Cl.⁵ .............................................. A61G 7/06
[52] U.S. Cl. ............................................ 5/632; 5/640; 5/644; 5/453; 128/200.24
[58] Field of Search ............... 128/28, 30, 30.2, 38, 128/200.24; 5/622, 631, 632, 636, 637, 640, 644, 453, 456, 652, 657

[56] References Cited

U.S. PATENT DOCUMENTS

| | | | |
|---|---|---|---|
| 3,326,601 | 6/1967 | Vanderbilt et al. | 5/453 |
| 3,330,598 | 7/1967 | Whiteside | 5/453 X |
| 3,605,138 | 9/1971 | Tucker | 5/456 X |
| 3,795,021 | 3/1974 | Moniot | 5/622 X |
| 3,804,082 | 4/1974 | Tarjan et al. | 128/28 X |
| 3,870,038 | 3/1975 | Arblaster | 128/28 |
| 4,194,501 | 3/1980 | Watt | 128/75 |
| 4,259,757 | 4/1981 | Watson | 5/637 |
| 4,346,298 | 8/1982 | Dixit | 5/622 X |
| 4,415,203 | 11/1983 | Cawley | 5/622 X |
| 4,528,981 | 7/1985 | Behar | 5/637 X |
| 4,732,144 | 3/1988 | Cunanan | 128/878 |
| 4,867,140 | 9/1989 | Hovis et al. | 128/24 R |
| 4,893,367 | 1/1990 | Heimreid et al. | 5/632 |
| 4,915,124 | 4/1990 | Sember, III | 5/453 X |
| 5,048,136 | 9/1991 | Popitz | 5/481 X |
| 5,142,720 | 9/1992 | Kelso et al. | 5/453 X |

OTHER PUBLICATIONS

"Difficulties in Tracheal Intubation", by Harmer et al., 1987, pp. 75-77.

Primary Examiner—Michael F. Trettel
Attorney, Agent, or Firm—Hamilton, Brook, Smith & Reynolds

[57] ABSTRACT

A positioning system provides for airway management of a supine subject. A number of bags are provided for supporting the head and lower neck/upper shoulders area of the subject. Once the bags are positioned under the subject, each bag is pressurized using a pressurized fluid source which is controlled by a mechanical controller. The mechanical controller comprises a number of mechanical switches for regulating the pressure in each bag. By manipulating the mechanical switches, the pressure in each bag is adjusted to align the subject's head and lower neck/upper shoulders area such that the mouth, pharynx and trachea are linearly aligned.

41 Claims, 2 Drawing Sheets

METHOD AND APPARATUS OF A POSITIONING SYSTEM FOR AIRWAY MANAGEMENT

BACKGROUND

Airway management in the medical field may be accomplised by a process known as intubation. The intubation process refers to the passage of a tube through the nose or mouth into the trachea for maintenance of the tracheal airway during anesthesia, for relief of an imperilled airway from any cause or for artificial respiration. Situations requiring intubation arise in the operating room, the emergency room, on the hospital floor or even in the field with emergency paramedical personnel.

Anatomical variations in a patient's upper airway make some intubation procedures more difficult than others. These difficult intubations are exaserbated by the supine position of the patient during the procedure. For example, a short-necked, emphysematous patient supine on a flat surface will offer an acute orotracheal angle making intubation difficult. In some cases, such difficulties are assessed in advance and estimations of optimal head and neck support are made. However, medical personnel frequently make such assessments during laryngoscopy, which is an inspection of the larynx by means of a laryngoscope. In these situations, a failed first attempt at intubation usually results in a scramble for extra pillows to alter position of the patient's head. During this potentially life threatening time, the patient may not be breathing on his own and is unventilated.

SUMMARY OF THE INVENTION

The present invention is a method and apparatus for airway management which provides a mechanically controlled positioning system for the alignment of a patient's head and neck so as to produce a linear alignment of the mouth, pharynx and trachea within seconds. In a preferred embodiment, the method and apparatus of the present invention may be used to effectuate tracheal intubation or bronchoscopy. Alternatively, the present invention may be used for the positioning of any part of a patient's body in a wide range of surgical procedures including a maternity procedure.

In accordance with the present invention, a pair of airtight bags which are preferably pneumatic bags are provided to support the head and lower neck/upper shoulders area of a supine patient. Each bag is linked to a pressurized fluid source via a mechanical controller. One bag is positioned under the occiput of the patient's head and the other bag is situated under the lower neck/upper shoulders area. A foam latex cushion which may be placed over each bag covers that side of the bag which contacts the patient. The distance between the bags may be maintained by a strap. An adhesive material, preferably comprising one half of a hook and loop connector may be attached to a portion of the strap. A strip of adhesive material, preferably comprising the other half of the hook and loop connector may be attached to the underside of each bag. Both bags are then affixed to the strap by the preferred hook and loop connector (i.e. Velcro TM), assuring a constant separation between the bags.

The pressurized fluid source which may be liquid or gas-based and which is controlled by a controller is used to inflate the bags. The pressurized fluid source may comprise a pump and a plenum chamber. In a preferred embodiment, the pump is a linear electrical motor-powered pump capable of delivering gas up to a maximum pressure of 300 Torr. The pump delivers pressurized gas into the plenum chamber which provides a fully pressurized reserve volume. The plenum chamber has a preferred volume which is comparable to the combined volume of the two bags. Thus, the combination of the high-pressure pump and plenum chamber effectuates the rapid delivery of a sufficient volume of high pressure gas to provide full inflation of the two bags within seconds. Furthermore, each bag will rise about five inches at full inflation from a fully deflated state allowing a wide range of positioning orientations.

Using the controller, the pressure in each bag is regulated so as to align the relative position of the patient's head and lower neck/upper shoulders area such that the mouth, pharynx and trachea are linearly aligned. The controller has interface ports which are connected to hoses from the bags as well as a hose from the the pressurized gas source thereby linking the bags to the pressure source. In a preferred embodiment of the present invention, the controller has only mechanical components and comprises two three-position mechanical switches to control the pressure in the two bags. Each switch has a first switch position corresponding to pressurization, a second switch position corresponding to maintaining a constant pressure and a third switch position corresponding to depressurization.

In a preferred system each mechanical switch is configured to control the pressure in one bag using a mechanical valve assembly comprising a pair of mechanical valves. Preferrably, the valves are spring-loaded pneumatic valves such as spool valves. The two valves within the assembly are connected in a series arrangement. Further, a first valve in the assembly controls pressure to the bags from the pressurized gas source, and a second valve of the assembly has a venting connection for controlling depressurization of the bags.

The above and other features of this invention including various novel details of construction will now be described with reference to the accompanying drawings and pointed out in the claims.

DETAILED DESCRIPTION OF THE INVENTION

Figure 1:
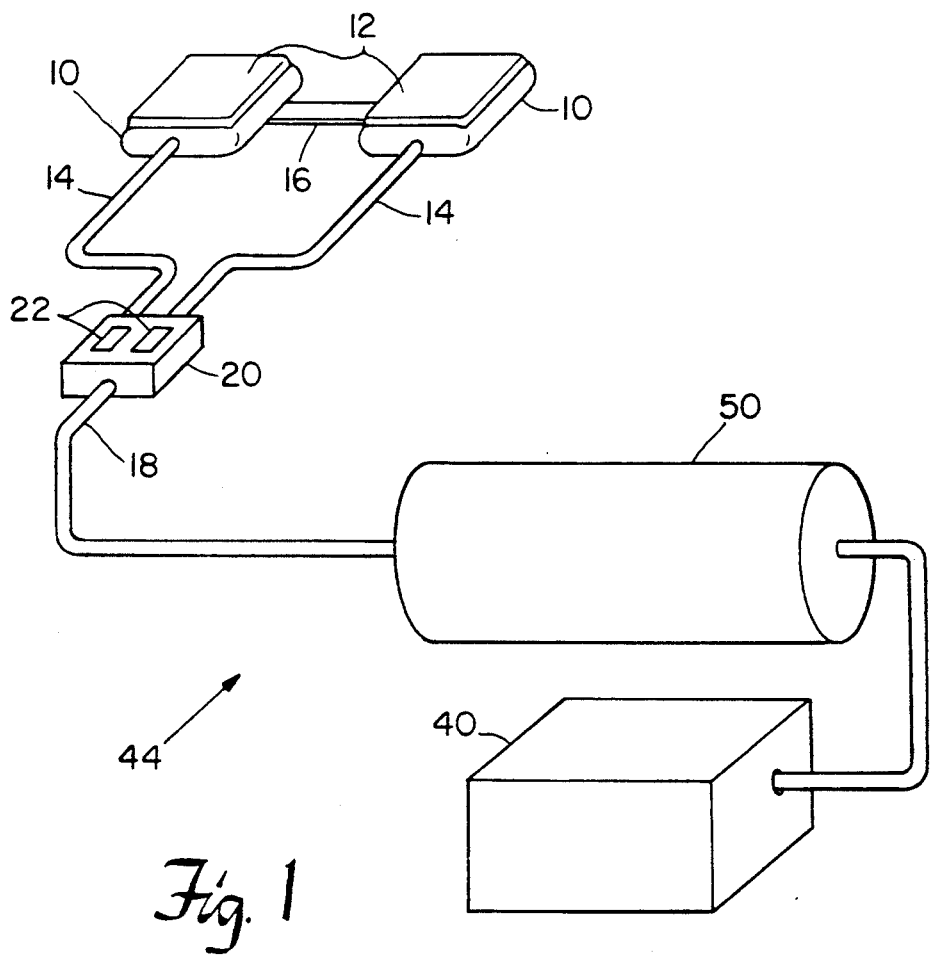
FIG. 1 illustrates a perspective view of a preferred embodiment of an airway management apparatus of the present invention.

A positioning system for airway management of a supine subject in accordance with the present invention is shown in FIG. 1. For any tracheal intubation, the head and low-- neck/upper shoulders area offer the only two points of freedom for alignment of the mouth, pharynx and trachea. Thus, proper adjustment of the relative position of the head to the lower neck/upper shoulders area is a critical prerequisite to the intubation procedure.

Accordingly, the positioning system of this invention may be used according to the following method for positioning of the subject's head and lower neck/upper shoulders area. A first bag 10 is positioned under the occiput of the subject's head, and an identical second bag 10 is positioned under the lower neck/upper shoulders area. Each bag is pressurized with fluid from a pressurized fluid source 44 as regulated by a controller 20. The pressure in each bag is then adjusted using a pair of mechanical switches 22 on the controller. Within seconds, the position of the head and lower neck/upper shoulders area are adjusted so as to produce a linear alignment 78 of the mouth 72, the pharynx 74 and the trachea 76 as shown in FIG. 2.

Figure 2:
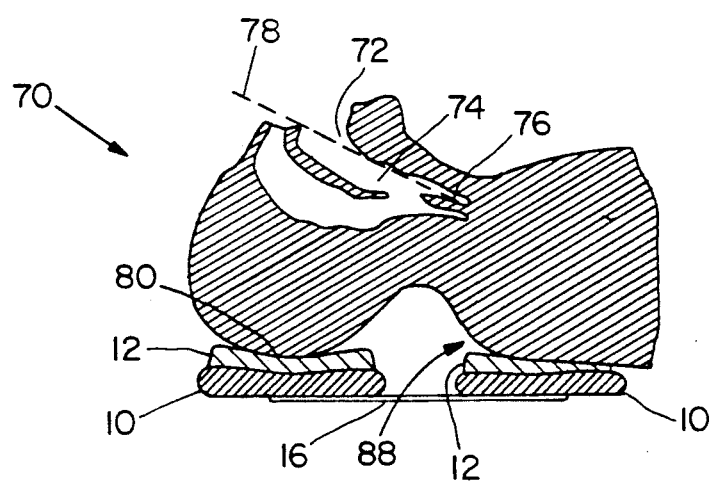
FIG. 2 is a sectional view of a supine subject disposed on a pair of bags which illustrates a linear alignment of the subject's airway.

In a preferred embodiment of the present invention, a pair of airtight bags 10 are used to support the occiput 80 of the head and lower neck/upper shoulders area 88 of a supine subject 70 shown in FIG. 2. Each bag is approximately five inches by twelve inches when fully deflated and is capable of rising five inches at full inflation. Further, each bag has a volume of about one and a half liters and may be filled with liquid or gas, though gas is preferred. The pressure rating for each bag is approximately 5 psi.

An adhesive strip such as one half of a hook and loop connector (Velcro TM) is attached to the underside of each bag 10. Once the two bags have been positioned under a subject, the distance between them is maintained using a strap. A strip of adhesive material 16, such as the other half of the hook and loop connector is attached to a portion of the strap. The strap allows different functional lengths to be selected between the bags 10. The adhesive feature ensures that neither bag moves out from under the patent during the positioning procedure.

Figure 3:
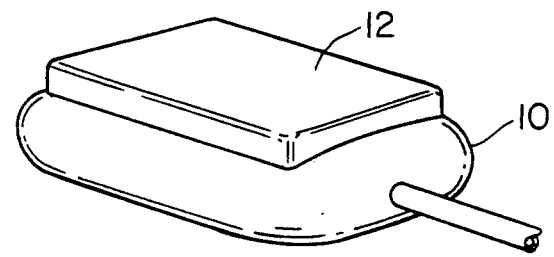
FIG. 3 is an enlarged perspective view of a bag of the present, invention.

A foam latex cover 12 is positioned on top of each bag 10 as shown in FIG. 3. The cover is sufficiently large to completely cover the side of the bag that encounters the subject 70. The the cover provides a soft, relatively flat surface upon which the subject may be placed without sliding off and which maintains a relatively stable shape during inflation and deflation of the bag. For sanitary purposes, the covers 12 may be replaceable and disposable.

A pressurized fluid source 44 is employed to pressurize the bags 10 in about five seconds, though preferably in two seconds, and comprises a pump 40 and a plenum chamber 50. The pump is a linear electrical motor-powered pump capable of continuous operation and pressure maintenance. The maximum deliverable pressure of the pump is about 300 Torr which approximately matches the rated pressure of the bags 10. The bags contain a pressure relief valve which ensures that the pressure in the bags does not exceed 5 psi. The pump 40 delivers pressurized gas to the plenum chamber 50. The plenum chamber serves as an integrator for the pressurized source and has a volume of about three liters which is equivalent to the volume of the two bags. This feature ensures that a reserve volume of fully pressurized gas is always available so that the system may operate continuously.

The pump 40 is capable of delivering pressurized gas at a rate of 40 liters per minute which equals 1.5 liters per two seconds. Since the the volume of the plenum chamber 50 is double the volume of each bag, the pressurized fluid source, including the pump and the pressurized plemun chamber, is capable of fully inflating both bags simultaneously in about two seconds. Thus, the position of the subject's head and lower neck/upper shoulder area can be adjusted quickly to produce a generally linear airway making intubation possible in seconds.

Figure 4:
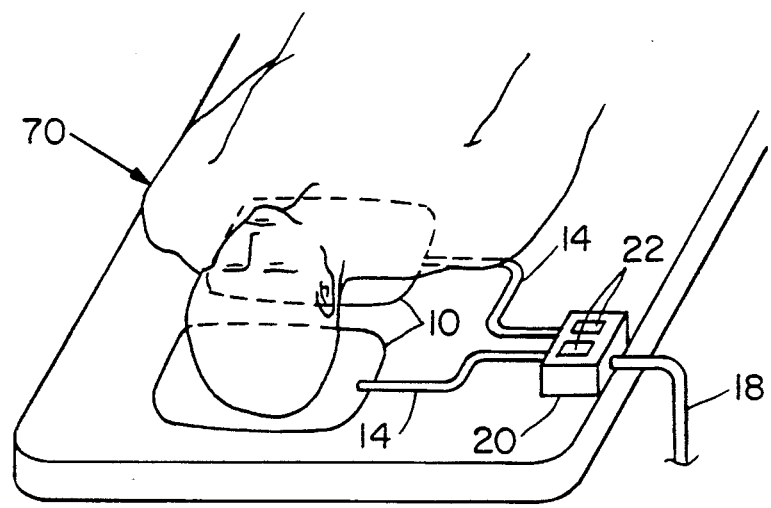
FIG. 4 illustrates a perspective view of a supine subject lying on a pair of bags connected to a controller.

A controller 20 couples the bags 10 to the pressurized source 44 for inflation and to the external environment for deflation. As shown in FIG. 4, the bags 10 are coupled to the controller 20 by a pair of hoses 14. Similarly, the pressurized gas source is coupled to the controller 20 by a hose 16. The pressure within each bag is adjusted by manipulating one of two three-position mechanical switches 22 on the controller 20. Each switch has a first switch position for pressurizing the corresponding bag, a second switch position for maintaining a constant pressure within the bag and a third switch position for depressurizing the bag.

The controller may be conveniently positioned next to the patient, where the physician controls the present invention with one hand while manipulating a laryngoscope with the other hand. The pressurized fluid source may be positioned out of the physician's way such as under the operating table. Alternatively, the pressurized fluid source may be a central pressurized air supply having a wall connection port.

For some surgical procedures, an assistant may be required to adjust the position of the patient periodically during the procedure. Since the present invention may be operated using only one hand, the assistant's other hand remains sterile. Thus, the assistant may actively assist the physician with his sterile hand during the surgical procedure.

Figure 5:
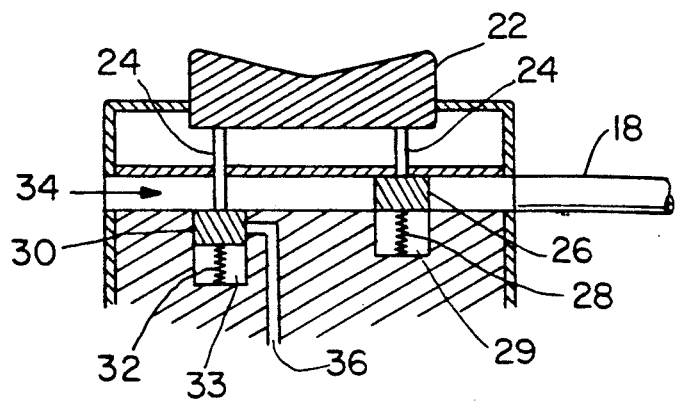
FIG. 5 is a schematic sectional view of a three-position mechanical switch connected to a pair of mechanical valves.

Each mechanical switch 22 is configured to control the pressure in one bag using two valves 26 and 28 as shown in FIG. 5. In a preferred embodiment, the valves are spring-loaded pneumatic valves such as spool valves. Thus, valve 26, for example, comprises a spring 28 and a valve chamber 29. Each pair of valves is connected in series through a mechanical switch 22 and controls the gas flowing through the conduit 34. For each pair of valves, a first valve 26 is used to effectuate pressurization of an associated bag and a second valve 30 is used to allow depressurization of the bag.

Each pair of valves is mechanically linked to a switch 22 by connecting rods 24. As shown in FIG. 5, the switch 22 is normally at the second switch position where the bag is isolated from the external environment and the pressurized source. At the second switch position, the first valve 26 resides in conduit 34 to prevent pressurized gas from entering the bag, and the second valve seals hole 36 to prevent gas in the bag from escaping into the external environment. Consequently, selecting the first switch position by depressing the right side of switch 22 moves the first valve 26 into valve chamber 29 by compressing spring 28. The second valve 30 is not affected by selecting the first switch position. With valve 26 positioned in its chamber 29, a coupling path is formed between the pressurized source and a bag through conduit 34 for pressurizing the bag. Releasing switch 22 from the first position causes the first valve 26 to return to its original position in conduit 2 which halts pressurization. Similarly, selecting the third switch position by depressing the left side of switch 22 moves the second valve ˆˆ into valve chamber 33 after compressing spring 32. First valve 26 is unaffected by the second switch position thereby isolating the pressurized source from the bag. With valve 30 positioned in the bottom of the valve chamber 33, a coupling path is formed between the bag and the external environment through vent hole 36 for depressurizing the bag. Releasing switch 22 from the third switch position allows valve 30 to return to its original position thereby sealing the hole 36.

One feature of the present invention is that the controller has no electrical parts and few moving parts. Functioning with strictly mechanical components, the controller operates safely without electricity. This feature is extremely significant in medical procedures, where it is normally desirable to keep electricity as far away from the patient as possible. Having very few moving parts, the controller operates with high reliability.

While this invention has been particularly shown and described with reference to specific preferred embodiments, it should be understood that those skilled in the art would be capable of devising various changes in form and detail without departing from the spirit and scope of the invention. For example, the valves are shown schematically for clarity of description but would preferrably be spool valves. Although a pair of valves supports each mechanical switch, alternatively a single valve may support a switch. Moreover, the spring element may be located in the switch assembly rather than in the valve assembly. Furthermore, other variations of the embodiment described herein will be apparent to those skilled in the art. Thus, the present invention is not to be limited to the positioning of the head and neck of a supine subject since it may be used to position other anatomical areas of a supine subject in a wide range of surgical procedures. For example, the present invention may be employed to position a subject's abdomen for a maternity procedure.

I claim:

1. A method of angulating the head and neck of a supine subject for airway management comprising:
   providing a number of pneumatic bags for supporting the head and lower neck/upper shoulders area of the subject, a controller for controlling the pressure within the bags, and a pressurized fluid source supplying fluid to the bags via the controller;
   positioning a first bag under the head of the supine subject and a second bag under the subject's lower neck/upper shoulders area;
   pressurizing the first and second bags with fluid wherein the pressure in each bag is adjusted using the controller to align the subject's head and lower neck/upper shoulder area such that the mouth, pharynx and trachea are linearly aligned.

2. A method of angulating the head and neck of a supine subject for airway management as claimed in claim 1 wherein the controller comprises a number of three-position mechanical switches having mechanical linkage to a number of mechanical control valves which control the coupling from the bags to the pressurized fluid source and to an external environment.

3. A method of angulating the head and neck of a supine subject for airway management as claimed in claim 2 in which adjusting the pressure in the first and second bags further comprises depressing a first three-position mechanical switch to regulate the pressure in the first bag and a second three-position mechanical switch to regulate the pressure in the second bag, wherein each switch has a first switch position corresponding to pressurization, a second switch position corresponding to maintaining a constant pressure and a third switch position corresponding to depressurization.

4. A method of angulation as claimed in claim 1 wherein each bag is airtight and comprises:
   a foam cushion attached to the side of the bag which contacts the subject; and
   a strip of adhesive material attached to the opposite side of the bag.

5. A method of angulation as claimed in claim 4 further comprising attaching the first and second bags to a strap having a strip of adhesive material attached to a portion thereof.

6. A method of angulation as claimed in claim 5 wherein the strip of adhesive material is one half of a hook and loop connector.

7. A method of angulation as claimed in claim 1 further comprising joining the first and second bags to a strap of adjustable functional length.

8. A method of positioning the head and neck of a supine subject for tracheal intubation comprising:
   providing a pair of pneumatic bags for supporting the head and lower neck/upper shoulders area of the subject, a controller for controlling the pressure in the bags and comprising a pair of three position mechanical switches having mechanical linkage to a number of control valves which are coupled to a pressurized gas source and an external environment wherein each mechanical switch has a first switch position corresponding to pressurization, a second switch position for maintaining a constant pressure and a third switch position corresponding to depressurization, and a pressurized gas source comprising a pump and a plenum chamber for supplying gas to the bags via the controller;
   positioning a first bag under the occiput of the subject's head and a second bag under the subject's lower neck/upper shoulders area;
   inflating the first and second bags with gas from the pressurized gas source regulated by the controller thereby altering the relative position of the subject's head and lower neck/upper shoulders area; and
   regulating the pressure in each bag within two seconds using the two mechanical switches on the controller in order to adjust the relative position of the head and lower neck/upper shoulder area so as to produce a linear alignment of the subject's oral cavity, pharynx and trachea.

9. A method of angulation as claimed in claim 8 wherein each bag is airtight and comprises a foam cushion over the side which contacts the subject and a strip of adhesive material attached to the opposite side of the bag.

10. A method of angulation as claimed in claim 9 further comprising attaching the first and second bags to a strap having adhesive material covering a portion of its length to maintain a constant separation of the two bags.

11. A method of angulation as claimed in claim 10 wherein the adhesive material is a hook and loop connector material.

12. A method of angulation as claimed in claim 8 further comprising attaching the bags to a strap of adjustable length.

13. A positioning system for airway management of a supine subject comprising:

a number of inflatable bags to be placed under the head and lower neck/upper shoulder area of the subject;

a strap of adjustable functional length upon which each bag is attached for providing a fixed separation between the bags for placement of the bags under the head and lower neck/upper shoulder area of the subject;

a pressurized fluid source for supplying fluid to the bags, the pressurized fluid source comprising a pump capable of delivering continuous pressurized fluid and a plenum chamber into which the pump delivers pressurized fluid for providing a fully pressurized preserve volume; and a controller for controlling the pressure in the bags and which comprises a number of mechanical switches corresponding to the number of bags and a number of mechanical valve assemblies wherein each valve assembly is mechanically linked to a mechanical switch and wherein each valve assembly controls coupling from a bag to the pressurized fluid source for pressurization of the bag and wherein each valve assembly also has a venting port for controlling depressurization of the bag.

14. A positioning system for airway management of a supine subject comprising:

a number of inflatable bags which are to be placed under the head and lower neck/upper shoulder area of the subject wherein a first inflatable bag is placed under the subject's head and a second inflatable bag is placed under the subject's lower neck and upper shoulder area, each bag comprising a foam cushion placed on a surface of the bag which contacts the subject, a strip of adhesive material attached to a surface opposite the surface upon which the cushion is placed and a hose which connects the bag to the controller;

a pressurized fluid source for supplying fluid to the bags, the pressurized fluid source comprising a pump capable of delivering continuous pressurized fluid and a plenum chamber into which the pump delivers pressurized fluid for providing a fully pressurized reserve volume; and a controller for controlling the pressure in the bags and which comprises a number of mechanical switches corresponding to the number of bags and a number of mechanical valve assemblies wherein each valve assembly is mechanically linked to a mechanical switch and wherein each valve assembly controls coupling from a bag to the pressurized fluid source for pressurization of the bag and wherein each valve assembly also has a venting port for controlling depressurization of the bag.

15. A head positioning system as claimed in claim 14 further comprising a strap having an adhesive material on a portion of its length upon which the first bag and the second bag are attached.

16. A positioning system as claimed in claim 15 wherein the controller further comprises:

three hose connection ports which accept the hoses from the first and second bags and a hose from the pressurized fluid source thereby coupling the bags to the pressurized fluid source;

a pair of three-position mechanical switches configured so that each switch controls one bag wherein each switch is mechanically linked to a mechanical valve assembly and wherein each switch has a first switch position corresponding to pressurization, a second switch position corresponding to maintaining a constant pressure and a third switch position corresponding to depressurization.

17. A positioning system as claimed in claim 16 wherein the controller further comprises two mechanical valve assemblies, wherein each assembly has two mechanical valves connected in a series, wherein the first valve of each pair controls coupling from a bag to the pressurized fluid source such that depressing the first switch position of an associated switch mechanically moves the first valve so as to couple the pressurized fluid source to the bag for pressurizing the bag, and wherein each pair of valves is configured such that selecting the second switch position isolates the bag from the controller to maintain constant pressure in the bag, and wherein the second valve of each pair controls coupling of the bag to an external environment such that depressing the third switch position mechanically moves the valve so as to connect the bag to the external environment for depressurizing the bag.

18. A positioning system as claimed in claim 16 wherein the mechanical value assemblies each comprise a mechanical valve wherein depressing the first switch position of a switch mechanically moves an associated valve whereby the valve couples the pressurized fluid source to a bag for pressurizing the bag, and wherein the valve is configured such that selecting the second switch position isolates the bag from the controller to maintain constant pressure in the bag, and wherein depressing the third switch position mechanically moves the valve whereby the valve couples the bag to the external environment for depressurizing the bag.

19. A positioning system as claimed in claim 17 wherein the mechanical valves are spring-loaded pneumatic valves.

20. A positioning system as claimed in claim 15 wherein the pressurized fluid source contains pressurized gas.

21. A positioning system as claimed in claim 20 in which the pressurized fluid source comprises:

a pump capable of delivering continuous pressurized gas; and a plenum chamber into which the pump delivers pressurized gas in order to provide a fully pressurized reserve volume.

22. A positioning system as claimed in claim 21 wherein the pump is a linear electrical motor powered pump.

23. A positioning system as claimed in claim 22 wherein the pump delivers a maximum gas pressure of no greater than 300 Torr.

24. A positioning system as claimed in claim 21 wherein the plenum chamber has a volume which is comparable to the combined volume of the first and second bags.

25. A positioning system as claimed in claim 24 wherein each of the first and second bags rises about five inches at full inflation from a fully deflated state.

26. A positioning system as claimed in claim 21 wherein the pump and plenum chamber are adapted to fully inflate the first and second bags in about two seconds.

27. A positioning system for tracheal intubation of a supine subject comprising:

a pair of pneumatic bags to be placed under the head and lower neck/upper shoulder area of the subject;

a strap of adjustable functional length upon which each bag is attached for providing a fixed separation between the bags for placement of the bags under the head and lower neck/upper shoulder area of the subject;

a pressurized gas source which supplies gas to the bags; and a controller which comprises two three-position mechanical switches for controlling pressure in the pneumatic bags and wherein each mechanical switch has a first switch position corresponding to pressurization, a second switch position corresponding to maintaining a constant pressure and a third switch position corresponding to depressurization, and two mechanical valve assemblies wherein each valve assembly has a pressure port for coupling a respective bag to the pressurized gas source and a venting port for coupling the respective bag to an external environment and wherein each valve assembly is mechanically linked to one of said mechanical switches such that the selection of the first switch position of a mechanical switch moves the valve assembly to a position which enables the pressure port to couple the pressurized gas source to the corresponding bag for pressurization and the selection of a second switch position of the mechanical switch configures the valve assembly so as to isolate the bag from the controller to maintain a constant pressure and the selection of a third switch position of the mechanical switch moves the valve assembly to a position which enables the venting port to couple the bag to the external environment for depressurization.

28. A positioning system as claimed in claim 27 wherein each mechanical valve assembly comprises a pair of spool valves wherein each pair of valves is connected in series whereby a first valve of each pair has a pressure port for coupling a bag to the pressurized source and whereby a second valve of each pair has a venting port for coupling a bag to the external environment.

29. A positioning system as claimed in claim 27 wherein the pressurized gas source is adapted to fully inflate the first and second bags in less than five seconds.

30. A positioning system as claimed in claim 29 wherein each of the first and second bags rises about five inches at full inflation from a fully deflated state.

31. A positioning system as claimed in claim 27 wherein the mechanical valve assemblies each comprise a pair of spring-loaded pneumatic valves.

32. A positioning system as claimed in claim 27 in which the pressurized gas source comprises:

a linear electrical motor-powered pump capable of delivering continuous pressurized gas; and a plenum chamber into which the pump delivers the pressurized gas in order to provide a fully pressurized reserve volume.

33. A positioning system as claimed in claim 32 wherein the pump delivers a maximum gas pressure of up to 300 Torr.

34. A positioning system as claimed in claim 27 wherein each bag is airtight and comprises:

a foam cushion which attaches to one side of the bag; and a strip of adhesive material which attaches to the side of the bag opposite the cushion.

35. A positioning system as claimed in claim 34 further comprising a strap having adhesive material along a portion of its length upon which the first and second bags are attached.

36. A positioning system for tracheal intubation of a supine subject comprising:

a pair of pneumatic bags which are placed under the head and lower neck/upper shoulder area of the subject wherein each pneumatic bag comprises a foam cushion which attaches to a surface of the bag, a strip of hook and loop connector material which attaches to a surface of the bag opposite the surface upon which the cushion attaches and a hose which connects the bag to a controller;

a pressurized gas source which supplies gas to the bags via the controller and which comprises a pump capable of delivering continuous pressurized gas and a plenum chamber into which the pump delivers the pressurized gas thereby providing a fully pressurized reserve volume; and a mechanical controller which controls pressure in the pneumatic bags and which comprises two three-position mechanical switches and two mechanical valve assemblies wherein each valve assembly has a pressure port for regulating coupling of a bag to the pressurized gas source and a venting port for regulating coupling of the bag to an external environment, and wherein each valve assembly is mechanically connected to one of said mechanical switches such that selecting a first switch position of the mechanical switch moves the associated first valve assembly by moving a spring mechanism within said valve assembly to a position whereby the pressure port couples the pressurized gas source to the bag via the mechanical controller for pressurizing the bag and such that selecting a second switch position of the mechanical switch isolates the bag from the mechanical controller and preserves a constant pressure in the bag and such that selecting a third switch position of the mechanical switch moves the second valve assembly by moving the spring mechanism within the valve assembly to a position whereby the venting port couples the bag to the external environment via the mechanical controller for depressurizing the bag.

37. A positioning system as claimed in claim 36 wherein each mechanical valve assembly comprises a pair of spring-loaded pneumatic valves wherein a first valve of each pair has a pressure port for coupling a bag to the pressurized source and wherein a second valve of each pair has a venting port for coupling a bag to the external environment.

38. A positioning system as claimed in claim 36 wherein the pump is a linear electrical motor-powered pump which delivers a maximum gas pressure no greater than 300 Torr.

39. A positioning system as claimed in claim 38 wherein the first and second bags rise about five inches from a fully deflated state to a fully inflated state.

40. A positioning system as claimed in claim 39 wherein the pump and plenum chamber are adapted to fully inflate the first and second bags in about two seconds.

41. A positioning system for positioning of a supine subject comprising:

a number of inflatable bags placed under the body of the subject;

a strap of adjustable functional length upon which each bag is attached for providing a fixed separation between the bags for placement of the bags under the subject;

a pressurized fluid source which supplies fluid to the bags; and a controller for controlling the pressure in the bags and which comprises a number of mechanical switches corresponding to the number of bags and a number of mechanical valve assemblies wherein each valve assembly is mechanically linked to a mechanical switch and wherein each valve assembly controls coupling from a bag to the pressurized source of pressurization of the bag and wherein each valve assembly also has a venting port for controlling depressurization of the bag.

* * * * *